United States Patent [19]

Zaiger

[11] Plant 4,395

[45] Mar. 13, 1979

[54] PEACH TREE

[76] Inventor: Chris F. Zaiger, 537 Rosemore Ave., Modesto, Calif. 95351

[21] Appl. No.: 862,634

[22] Filed: Dec. 20, 1977

[51] Int. Cl.[2] ..... A01H 5/03
[52] U.S. Cl. ..... Plt./43
[58] Field of Search ..... Plt./43

*Primary Examiner*—Robert E. Bagwill
*Assistant Examiner*—James R. Feyrer

[57] ABSTRACT

A new and distinct variety of peach tree which has the following unique combination of features that are outstanding in a new variety.

1. The small or dwarf size of the tree 7–9 feet at maturity.
2. The large size of the fruit.
3. The extreme firmness of the fruit and its good shipping characteristic.
4. The heavy and regular bearing of large, uniform fruit.
5. The variety being well adapted for growing both as an ornamental tree and for the production of fruit with good eating and shipping quality.

3 Drawing Figures

ORIGIN OF THE VARIETY

The herein variety of peach tree was originated by me in my experimental orchard located at Modesto, Stanislaus County, Calif., as follows: Seeds were gathered at random from seedling trees showing low growing, semi-dwarfism and dwarf characteristics in my experimental orchard. These seeds were planted and the seedlings grown and maintained under close observation by me, gave many and varying characteristics. One such seedling which is the present variety evidenced distinctive characteristics with respect to dwarf tree size and bearing of large, good quality fruit was selected for asexual reproduction and commercialization.

ASEXUAL REPRODUCTION OF THE VARIETY

The present variety of peach tree was asexually reproduced by budding, as performed at Modesto, Calif., shows that said characteristics come true to form and are established and transmitted through succeeding propagations.

SUMMARY OF THE VARIETY

The present variety relates to a new and distinct variety of dwarf peach tree of medium dense, upright growth which bears large size, firm, yellow flesh, freestone fruit. The new variety is also characterized by fruit with deep yellow skin color overspread with a red blush on fruits exposed to sun, uniform ripening, good flavor and shipping quality which makes this variety a desirable peach for the ornamental trade as well as for the commercial fruit industry. The foregoing characteristics and distinctions differentiate my new variety from all other varieties of which I am aware.

BRIEF DESCRIPTION OF THE DRAWING

The accompanying photographic illustrations show typical specimens of the foliage and fruit of my new variety, an exterior and sectional view of the fruit with the stone in place, and a small branch with the upper and lower surface of the foliage being illustrated. The photograph further illustrates the slight rough bark condition on the branches which is characteristic of the present variety.

DESCRIPTION OF THE VARIETY

The following is a detailed botanical description of the new and distinct variety of dwarf peach tree and its fruit, with color definitions (except those in common color terms) referenced to Reinhold Color Atlas, by A. Korneruf and J. H. Wanscher are based upon observations of specimens grown at Modesto, Calif.

Tree:
- *Size.*—Dwarf — 7 to 9 feet at maturity.
- *Vigor.*—Non-vigorous.
- *Density.*—Medium dense to dense.
- *Production.*—Productive.
- *Bearer.*—Regular.

Trunk:
- *Size.*—Stocky.
- *Texture.*—Shaggy.

Branches:
- *Size.*—Medium. Stocky to medium caliper in relationship to length.
- *Texture.*—Medium rough to rough. Medium shaggy.
- *Color.*—Brown to reddish brown.

Leaves:
- *Size.*—Medium. Average length when mature — $6\frac{3}{4}''$. Average width when mature — $1\frac{5}{8}''$.
- *Shape.*—Lanceolate. Tip acuminate. Medium thick.
- *Glands.*—Reniform. Medium size. Average number 4. Positioned on base of blade and petiole, usually alternate.
- *Margin.*—Crenate.
- *Petiole.*—Average length — 11/16". Average width — 1/16".
- *Color.*—Upper surface — dark green (27-F-8) to (28-F-7). Under surface — grayish green (28-D-8) to (29-E-7).

Flower buds:
- *Size.*—Medium size. Medium length.
- *Form.*—Plump.
- *Pubescence.*—Pubescent.

Flowers:
- *Size.*—Large — showy.
- *Blooming period.*—Feb. 25, 1977 to Mar. 10, 1977. Varies slightly with climatic conditions.
- *Pollen.*—Present.

*Color.*—Pink.

Fruit:

*Maturity when described.*—Hard ripe.

*Date of first picking.*—July 29, 1977.

*Date of last picking.*—Aug. 5, 1977.

*Size.*—Large. Average diameter axially — 3" to 3¼". Average transversely in suture plane — 3" to 3¼".

*Form.*—Globose. Nearly symmetrical.

*Suture.*—Shallow.

*Ventral surface.*—Rounder — slightly lipped.

*Base.*—Retuse.

*Cavity.*—Rounded. Average depth — ½". Average breadth — 1".

*Apex.*—Rounded to slight depression.

Skin:

*Thickness.*—Medium.

*Texture.*—Medium. Tenacious to flesh when firm ripe. Free when soft ripe.

*Tendency to crack.*—None.

*Down.*—Scant. Short.

*Color.*—Bright yellow ground color yellow to flame yellow (3-A-8) to (4-A-7). Red blush covering the surface exposed to sun light yellow red to coral red (8-A-7) to (9-B-7).

Flesh:

*Color.*—Yellow (3-A-7 to 3-A-8) except mottled with red next to stone grading from intense red next to pit (10-B-8 to 11-B-8) toward a lighter red (10-A-5 to 10-A-6) as the distance increases from the pit toward the skin.

*Surface of pit cavity.*—Mottled red becomes complete red when soft ripe.

*Texture.*—Firm and crisp.

*Fibers.*—Few.

*Amygdalin.*—Moderate.

*Ripens.*—Evenly.

*Flavor.*—Mild sub-acid.

*Aroma.*—Moderate.

*Eating quality.*—Good.

Stone:

*Type.*—Freestone.

*Size.*—Large. Average length — 1½". Average width — 1⅛" to 1¼". Average thickness — ¾".

*Form.*—Ovoid.

*Base.*—Straight to slightly oblique.

*Apex.*—Acute.

*Sides.*—Equal to unequal.

*Surface.*—Irregularly furrowed toward apex, pitted toward base.

*Ridges.*—Rounded toward base and middle.

*Tendency to split.*—None.

*Color.*—Light brown.

Use: Local and long distance markets. Dessert.

Keeping quality: Good.

Shipping quality: Good.

The tree and its fruit herein described may vary in slight detail due to climatic, soil conditions and cultural practices under which the variety may be grown; the present description being of the variety as grown by me in my experimental orchard at Modesto, Calif.

I claim:

1. A new and distinct variety of peach tree; as illustrated and described, characterized by its dwarf size, averaging 7 to 9 feet at maturity and further characterized by its productive and regular bearing of large size, yellow flesh, freestone fruit of good eating quality and the high degree of firmness of fruit when mature provides good shipping characteristics.

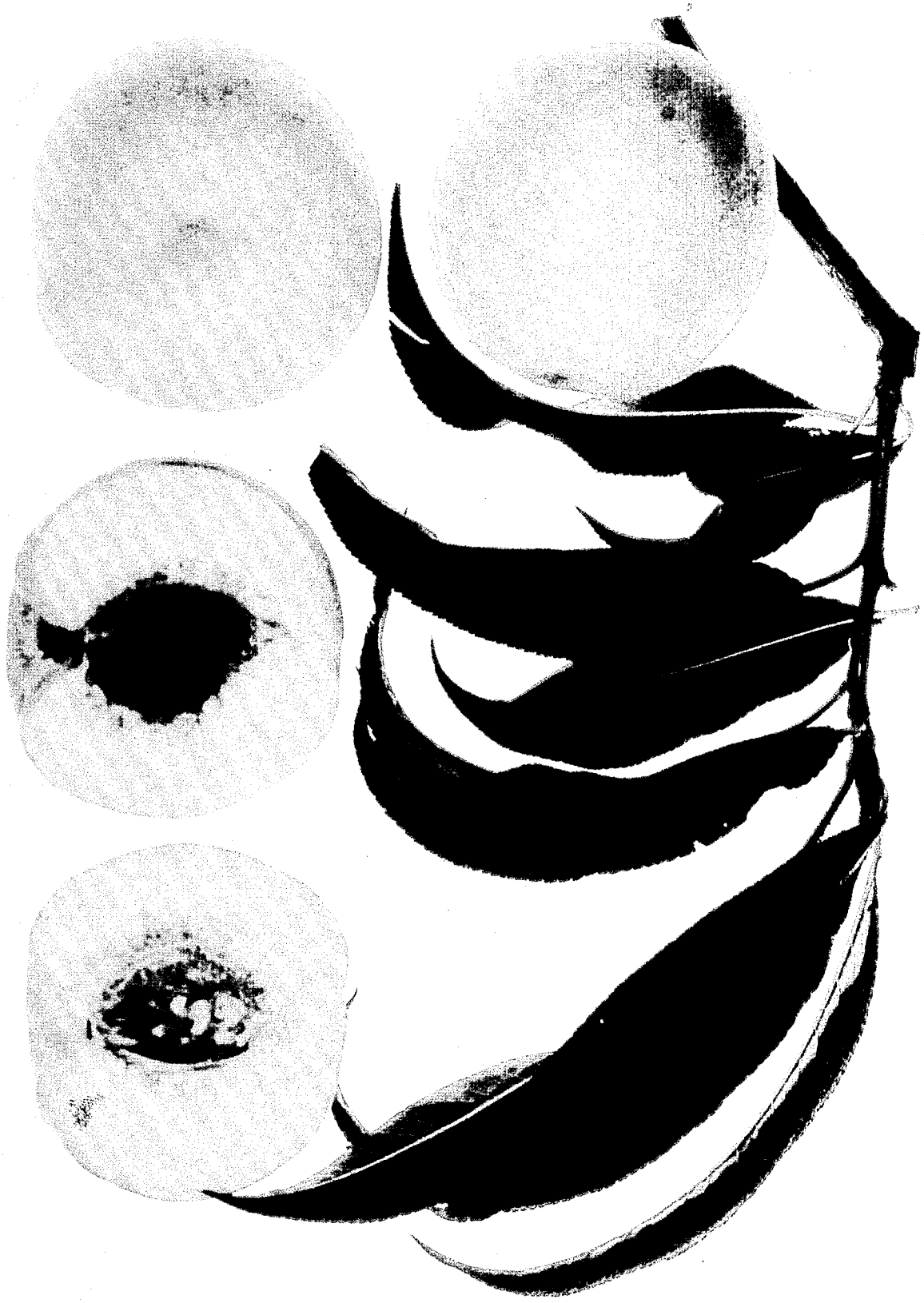

* * * * *